US011008328B2

(12) United States Patent
Da Costa Pereira Rosa et al.

(10) Patent No.: US 11,008,328 B2
(45) Date of Patent: May 18, 2021

(54) PROCESSES FOR THE PREPARATION OF PHARMACEUTICALLY ACCEPTABLE SALTS OF (R)-PIRLINDOLE AND (S)-PIRLINDOLE

(71) Applicant: TECNIMEDE, SOCIEDADE TÉCNICO-MEDICINAL, SA, Sintra (PT)

(72) Inventors: Carla Patrícia Da Costa Pereira Rosa, Sintra (PT); João Carlos Ramos Damil, Sintra (PT); Ana Vanessa Cordeiro Simões, Sintra (PT); João Pedro Silva Serra, Sintra (PT)

(73) Assignee: TECNIMEDE, SOCIEDADE TÉCNICO-MEDICINAL, SA, Sintra (PT)

( * ) Notice: Subject to any disclaimer, the term of this patent is extended or adjusted under 35 U.S.C. 154(b) by 0 days.

(21) Appl. No.: 16/607,051

(22) PCT Filed: Apr. 20, 2018

(86) PCT No.: PCT/IB2018/052756
§ 371 (c)(1),
(2) Date: Oct. 21, 2019

(87) PCT Pub. No.: WO2018/193415
PCT Pub. Date: Oct. 25, 2018

(65) Prior Publication Data
US 2020/0190098 A1 Jun. 18, 2020

(30) Foreign Application Priority Data

Apr. 21, 2017 (PT) .......................................... 110038
Apr. 24, 2017 (EP) ..................................... 17167852

(51) Int. Cl.
*C07D 487/22* (2006.01)
*C07D 487/06* (2006.01)

(52) U.S. Cl.
CPC ................. *C07D 487/06* (2013.01)

(58) Field of Classification Search
CPC ..................................................... C07D 487/22
USPC ........................................................... 544/343
See application file for complete search history.

(56) References Cited

U.S. PATENT DOCUMENTS 3,288,860 A 11/1966 Lyness

FOREIGN PATENT DOCUMENTS

| EP | 1044976 | 10/2000 |
| EP | 2597097 | 5/2013 |
| WO | 2015171003 | 11/2015 |
| WO | 2015171005 | 11/2015 |

OTHER PUBLICATIONS

N I Andreeva et al: "Molecular Biological Problems of the Creation of Drugs and Study of the Mechanism of Their Action: Synthesis and Pharmacological Properties of Pyrazidole Enantiomers", Pharmaceutical Chemistry Journal, vol. 26, No. 5, 1992, pp. 365-369.
Buckley et al., "Report on thermal reaction," Chemical & Engineering News, vol. 60, No. 28, 1982, p. 5.
Dewall et al., "Sodium Hydride and DMF," Chemical & Engineering News, vol. 60, No. 37, 1982, p. 5 and p. 43.
L.C. Cross and W. Klyne (collators), "Rules for the Nomenclature of Organic Chemistry. Section E: Stereochemistry (Recommendations 1974)," Pure & Applied Chemistry, vol. 45, 1976, pp. 11-30.
P. Yu Ivanov et al: "New approach to the synthesis of pyrazidol", Pharmaceutical Chemistry Journal, vol. 21, No. 1, Jan. 1, 1987 (Jan. 1, 1987), US, pp. 62-65.
A. I. Bokanov et al: "Synthesis of Heterocycles on the Basis of iminotetrahydrocarbazoles. 1. 3-Benzyl-8-Methyl-2-Oxo-2,3,3a,4,5,6-Hexahydro-IH-Pyrazino [3,2,1-j,k]", Chemistry of Heterocyclic Compounds, vol. 23, No. 12, Jan. 1, 1987 (Jan. 1, 1987), pp. 1311-1315.
A. V. Ivachtchenko et al, "New Heterocyclic Hepatitis C Virus (HCV) Inhibitors Containing A 2-Aminomethyl-1H-Indole Fragment", Pharmaceutical Chemistry Journal, vol. 49, No. 6, Sep. 1, 2015 (Sep. 1, 2015), p. 352-361.
International Search Report and Written Opinion dated Jun. 12, 2019 corresponding to International Patent Applicatio No. PCT/IB2018/052756; 10 pages.

*Primary Examiner* — Douglas M Willis
(74) *Attorney, Agent, or Firm* — Leason Ellis LLP

(57) ABSTRACT

The present invention relates to an improved process for the preparation of Pirlindole enantiomers, or a pharmaceutically acceptable salt thereof.

28 Claims, No Drawings

PROCESSES FOR THE PREPARATION OF PHARMACEUTICALLY ACCEPTABLE SALTS OF (R)-PIRLINDOLE AND (S)-PIRLINDOLE

CROSS-REFERENCE TO RELATED APPLICATIONS

This is a U.S. National Phase Application under 35 U.S.C. § 371 of International Application No. PCT/1132018/052756, filed Apr. 20, 2018, and claims priority to Portuguese (PT) Patent Application No. 110038, filed Apr. 21, 2017 and European Application No. 17167852.7, filed Apr. 24, 2017, all of which are hereby incorporated by reference in their respective entireties as if expressly set forth herein.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

Field of the Invention

The present invention relates to an improved process for the preparation of Pirlindole enantiomers, or a pharmaceutically acceptable salt thereof.

Description of Related Art

Pirlindole (8-methyl-2,3,3a,4,5,6-hexahydro-1H-pyrazino[3,2,1-jk]carbazole) of formula I Compound Formula I

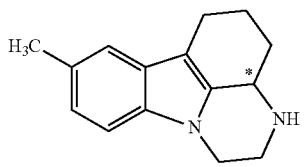

also described as Pyrazidole™ represents a new class of original tetracyclic antidepressants, the pyrazinocarbazole derivatives. The drug was synthesized and characterized at the end of the 1960s and was marketed as an anti-depressant in 1975. Current clinical trials have demonstrated to be a highly effective short-acting and safe drug.

Pirlindole is a selective, reversible inhibitor of MAO-A. In-vitro evidence suggest the catalytic oxidation of Pirlindole into dehydro-pirlindole by MAO-A. Dehydro-pirlindole may be a more potent slowly reversible inhibitor of MAO-A and this might explain the persistence of MAO-A inhibition in-vivo (MAO—The mother of all amine oxidases, John P. M. Finberg et al. 1998, Springer).

Pirlindole chemical structure is composed of one stereogenic centre which indicates the existence of two enantiomers, the (R)-Pirlindole and the (S)-Pirlindole.

Although Pirlindole pharmacological data and the clinical use were performed on the racemate, recently there have been increasing interest in the pharmacological profile of each enantiomer (WO 2015/171005 A1).

International patent publication WO 2015/171003A1 filed 9 May 2014 discloses a resolution of racemic pirlindole into optically active pirlindole. The Resolution-Racemization-Recycle (RRR) synthesis described involves derivatization by preparation of pairs of diastereomers in the form of salts from an optically active organic acid. These diastereomers can be separated by conventional techniques such as crystallisation. Although it is a very efficient procedure to prepare laboratorial scale or pre-clinical batch of (R)- or (S)-Pirlindole, it is not economically convenient at an industrial scale because the process relies on Pirlindole racemate as the starting material.

Andreeva et al. (*Pharmaceutical Chemistry* 1992, 26, 365-369) discloses the first isolation of Pirlindole enantiomers in isolated form. (R)-Pirlindole of formula II

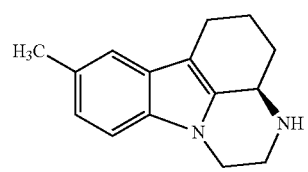

was isolated as an hydrochloride salt from a racemic base by the fractional crystallization of racemic pirlindole salt with (+)-camphor-10-sulfonic acid. (S)-Pirlindole formula III

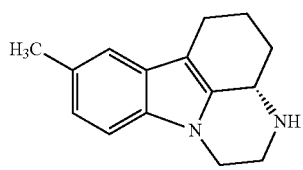

was also isolated as an hydrochloride salt although via asymmetric synthesis from the 6-methyl-2,3,4,9-tetrahydro-1H-carbazol-1-one IV

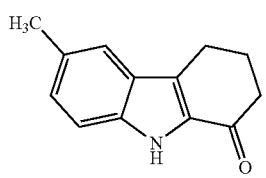

Compound of formula IV was reacted with chiral auxiliary (S)-(−)-α-methylbenzylamine to afford asymmetric (S)-6-methyl-N-(1-phenylethyl)-2,3,4,9-tetrahydro-1H-carbazol-1-imine V

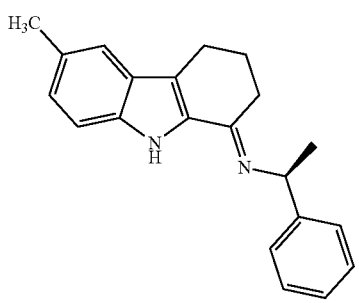

Compound of formula V was subjected to stereoselective reduction with sodium borohydride in ethanol. According to Andreeva et al. the reaction might occur through directed intramolecular hydride transfer after formation of a complex between compound of formula V and reducing agent to afford (S)-6-methyl-N—((S)-1-phenylethyl)-2,3,4,9-tetrahydro-1H-carbazol-1-amine VI

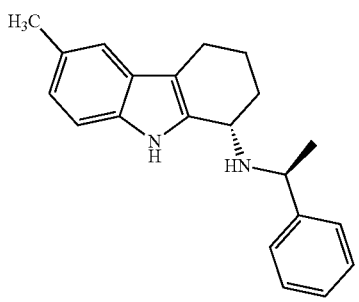

Compound of formula VI is reacted with ethylene glycol ditosylate by ethylene bridge formation under alkaline conditions to yield (S)-8-methyl-3-((S)-1-phenylethyl)-2,3,3a,4,5,6-hexahydro-1H-pyrazino[3,2,1-jk]carbazole VII.

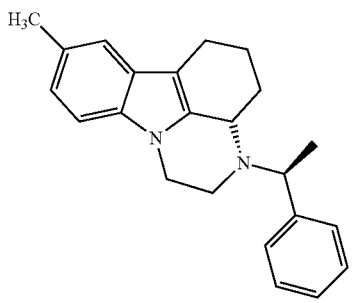

Alkaline agent is sodium hydride (NaH), in the presence of dimethyl sulfoxide (DMSO) or dimethylformamide (DMF).

The ratio between alkaline agent, compound of formula VI and ethylene glycol ditosylate is 1.2:1:1.

The cyclization reaction occurs at room temperature for a period of 4.5 hours.

Compound of formula VII was subjected to catalytic hydrogenolysis conditions to afford the desired hydrochloride salt of compound of formula III.

The hydrogenolysis reaction was catalysed by Palladium on charcoal (Pd content 0.1 g, 9 mol %) and was conducted in methanol. The conversion of compound of formula VII into compound of formula III was performed under a hydrogen pressure of 1.8-2.0 MPa at 22° C. for a period of 17 h.

The work-up conditions for the hydrogenolysis reaction involved neutralization with ammonia solution followed by benzene recrystallization. The hydrochloride salt of compound of formula III was formed from addition of hydrochloric acid to a solution of free base in ethanol.

The process yielded (S)-Pirlindole hydrochloride with a final yield of 10% with respect to the intermediate VI.

The mixture of sodium hydride with DMSO generates dimsyl anion. This anion is very often used in laboratory scale, but because it is unstable its use on large scale should be under specific precautions. Dimsyl anion decomposition is exothermic. It is reported that dimsyl anion decomposition starts even at 20° C., and above 40° C. it decomposes at an appreciable rate (Lyness, W. I. et al., U.S. Pat. No. 3,288,860 1966, Cl. 260-607).

The mixture of DMF and sodium hydride is reported in 'Sax & Lewis's Dangerous Properties of Industrial Materials' to give a violent reaction with ignition above 50° C. Buckey, J. et al., Chem. Eng. News 1982, 60(28), 5, describes the thermal runaway of a pilot plant reactor containing sodium hydride and DMF from 50° C. Accelerated Rate calorimetry (ARC) tests showed exothermic activity as low as 26° C. Similar behaviour was also seen with DMA. De Wall, G. et al., Chem. Eng. News 1982, 60(37), 5, reports a similar incident, wherein runaway started at 40° C., and rose 100° C. in less than 10 minutes, boiling off most of the DMF.

There exists a need for safe, industrial- and eco-friendly processes for the preparation of Pirlindole enantiomers. These facts are disclosed in order to illustrate the technical problem addressed by the present disclosure.

BRIEF SUMMARY OF THE INVENTION

The process disclosed herein provides an industrially applicable synthesis of pirlindole enantiomers or pharmaceutically acceptable salts thereof. The present disclosure relates to the transformation of compound of formula VI ((S)-6-methyl-N—((S)-1-phenylethyl)-2,3,4,9-tetrahydro-1H-carbazol-1-amine) into compound of formula VII ((S)-8-methyl-3-((S)-1-phenylethyl)-2,3,3a,4,5,6-hexahydro-1H-pyrazino[3,2,1-jk]carbazole) can be conducted in dipolar aprotic solvent such as 1,3-dimethyl-2-imidazolidinone (DMI). The advantages of using DMI with a suitable alkaline agent, in particular DMI with sodium hydride (NaH) are the following: DMI is thermally stable towards NaH and as such this mixture may be heated up in safe conditions, which leads to increased conversion rates and reaction yields of, for example, compound of formula VI into the compound of formula VII (see Tables 1 and 2). The work-up of this reaction involves addition of methanol (MeOH) to precipitate the compound of formula VII. As DMI is very soluble in dichloromethane (DCM), the extraction of the mother liquor with dichloromethane allows the recovery of DMI that can be later re-used.

The catalytic hydrogenolysis of compound of formula VII obtained by this process produces high purity crude compound of formula III ((S)-pirlindole) requiring simple purification steps, as no basification is necessary.

The present disclosure relates to a process for the synthesis of pirlindole enantiomers of formula II and III

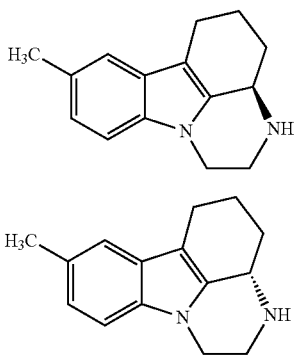

II

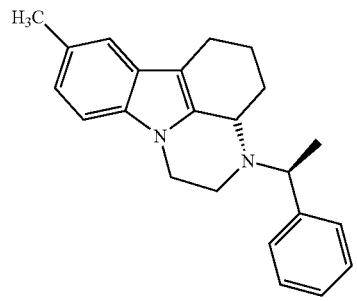

VII

III

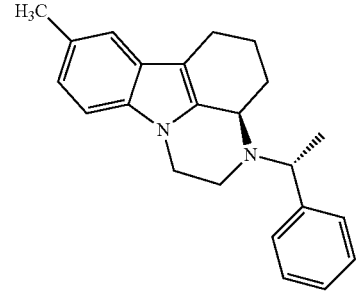

IX or a pharmaceutically acceptable salt thereof, comprising the steps of:

cyclization between compound of formula VI (S)-6-methyl-N—((S)-1-phenylethyl)-2,3,4,9-tetrahydro-1H-carbazol-1-amine or its enantiomer compound formula VIII (R)-6-methyl-N—((R)-1-phenylethyl)-2,3,4,9-tetrahydro-1H-carbazol-1-amine

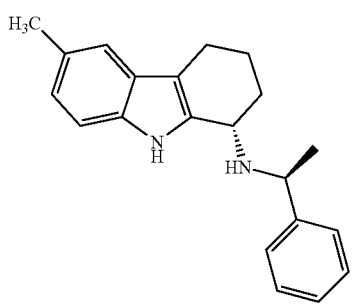

VI

VIII and compound of formula X

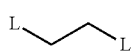

X wherein L is a leaving group selected from —OTs, —OMs, —OTf, —Cl or —Br, —I in 1,3-dimethyl-2-imidazolidinone (DMI), in the presence of a suitable alkaline agent to yield (S)-8-methyl-3-((S)-1-phenylethyl)-2,3,3a,4,5,6-hexahydro-1H-pyrazino[3,2,1-jk]carbazole VII or enantiomer (R)-8-methyl-3-((R)-1-phenylethyl)-2,3,3a,4,5,6-hexahydro-1H-pyrazino[3,2,1-jk]carbazole IX and subjecting compound of formula VII or IX to a catalytic hydrogenolysis. Unexpectedly, the use of DMI provides a significant increase in the yield of the process now disclosed and also on the reaction conversion of compound VI or VIII into compound VII or IX, respectively.

In an embodiment and to obtain even better results, the molar ratio of the suitable alkaline agent:intermediate VI or VIII:compound of formula X may be from 1:1:1 to 5:1:3. More in particular the molar ratio 1:1:1; 1:1:1.2; 1:1:1.5; 1:1:2; 1:1:3; 1.2:1:1; 1.2:1:1.2; 1.2:1:1.5; 1.2:1:2; 1.2:1:3; 2.2:1:1; 2.2:1:1.2; 2.2:1:1.5; 2.2:1:2; 2.2:1:3; 2:1:1; 2:1:1.2; 2:1:1.5; 2:1:2; 2:1:3; 3:1:1; 3:1:1.2; 3:1:1.5; 3:1:2; 3:1:3; 4:1:1; 4:1:1.2; 4:1:1.5; 4:1:2; 4:1:3; 5:1:1; 5:1:1.2; 5:1:1.5; 5:1:2; 5:1:3.

In an embodiment and to obtain even better results, the molar ratio of the suitable alkaline agent:intermediate VI or VIII: compound of formula X may be from 2.2:1:1.2 to 4:1:2, preferably from 3:1:1.2 to 4:1:1.5, even more preferably from 3:1:1.2 to 4:1:1.2.

In an embodiment and to obtain even better results, the molar ratio of the suitable alkaline agent:intermediate VI or VIII:compound of formula X may be 4:1:2.

In an embodiment and to obtain even better results, the suitable alkaline agent may be sodium hydride.

In an embodiment and to obtain even better results, L of the compound of formula X may be preferably —OTs.

In an embodiment and to obtain even better results, the pharmaceutically acceptable salt of Pirlindole enantiomer III or II may be acetate salt, hydrochloride salt, hydrobromide salt, mandelate salt, citrate salt, succinate salt, tartrate salt, malonate salt, maleate salt, methanesulfonate salt, lactate salt, ethanesulfonate salt, glutamate salt or phosphate salt.

In an embodiment and to obtain even better results, the pharmaceutically acceptable salt may be hydrochloride salt or methanesulfonate salt.

In an embodiment and to obtain even better results, the pharmaceutically acceptable salt may be pharmaceutically acceptable salt is lactate salt, ethanesulfonate salt, mandelate salt, citrate salt or succinic salt.

In an embodiment and to obtain even better results, the step of cyclization between compound of formula VI (S)-6-methyl-N—((S)-1-phenylethyl)-2,3,4,9-tetrahydro-1H-carbazol-1-amine, or its enantiomer compound formula VIII (R)-6-methyl-N—((R)-1-phenylethyl)-2,3,4,9-tetrahydro-1H-carbazol-1-amine, and compound of formula X, may be carried out at temperatures between 50° C. and 120° C., preferably at 60° C.

In an embodiment and to obtain even better results, the catalytic hydrogenolysis may be carried out at temperatures between 20-70° C., preferably at 50° C.

In an embodiment and to obtain even better results, the catalytic hydrogenolysis may be carried out for 2-8 hours, preferably 5 hours.

BRIEF DESCRIPTION OF THE SEVERAL VIEWS OF THE DRAWINGS

Not Applicable.

DETAILED DESCRIPTION OF THE INVENTION

The present invention provides a process for the synthesis of Pirlindole enantiomers which are readily convertible to the corresponding acid salts.

In one embodiment, the process of the present invention uses the intermediate compound of formula VI, (S)-6-methyl-N—((S)-1-phenylethyl)-2,3,4,9-tetrahydro-1H-carbazol-1-amine.

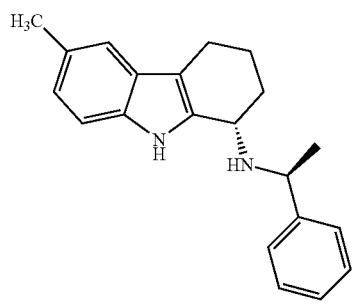

VI

Compound of formula VI can be prepared in two steps: 1-condensation of compound of formula IV, 6-methyl-2,3,4,9-tetrahydro-1H-carbazol-1-one

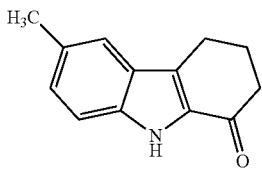

IV with chiral auxiliary (S)-(−)-α-methylbenzylamine, followed by: 2-stereoselective reduction with sodium borohydride.

Compound of formula VI can cyclize to yield compound of formula VII, (S)-8-methyl-3-((S)-1-phenylethyl)-2,3,3a,4,5,6-hexa hydro-1H-pyrazino[3,2,1-jk]carbazole

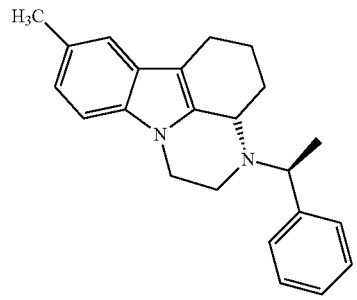

VII which can be subjected to catalytic hydrogenolysis to afford compound formula III (5)-Pirlindole.

In one embodiment, the present invention relates to the preparation of (R)-Pirlindole of formula II. Wherein enantiomer of compound formula VI, (R)-6-methyl-N—((R)-1-phenylethyl)-2,3,4,9-tetrahydro-1H-carbazol-1-amine VIII

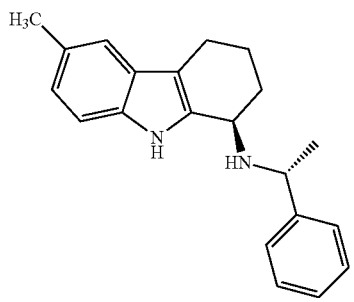

VIII is obtained from condensation of compound formula IV with (R)-(+)-α-methylbenzylamine. Compound of formula VIII can cyclize to yield compound of formula IX

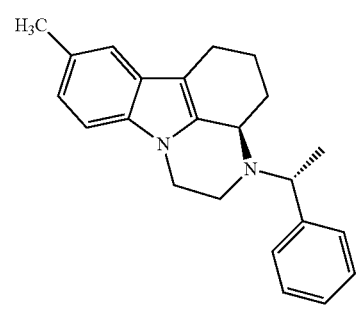

IX which can be subjected to catalytic hydrogenolysis to afford compound formula II (R)-Pirlindole.

In an embodiment, the present invention relates to a cyclization reaction producing intermediate compound of formula VII, (S)-8-methyl-3-((S)-1-phenylethyl)-2,3,3a,4,5,6-hexahydro-1H-pyrazino[3,2,1-jk]carbazole.

In an embodiment, compound of formula VI is reacted with compound of formula X wherein L is a leaving group in a suitable solvent and in the presence of a suitable alkaline agent.

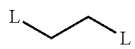

In an embodiment, examples of leaving groups include, but are not limited to, sulfonic alcohols such as —OTs, —OMs, —OTf, or halogens such as —Cl, Br, —I, preferably L is —OTs.

In an embodiment, compound of formula X is ethane-1, 2-diyl bis(4-methylbenzenesulfonate).

In an embodiment, compound of formula X can be prepared in situ from ethylene glycol in the presence of a suitable reagent, for example, one selected from the group consisting of thionyl chloride, sulfonyl halides, such as sulfonyl chloride, sulfonyl anhydride and phosphorous halides. Preferably the reagent is selected from the group consisting of thionyl chloride, p-toluenesulfonyl chloride, methanesulfonyl chloride, methanesulfonic anhydride, p-toluenesulfonic anhydride, trifluoromethanesulfonic anhydride, phosphoryl chloride, phosphorous tribromide and phosphorous pentachloride. More preferably the reagent is p-toluenesulfonyl chloride.

In an embodiment, the suitable alkaline agent according to the invention is selected from, but it is not limited to, a carbonate or hydride of an alkali metal salt such as caesium carbonate or sodium hydride, or even a phosphate salt of alkali metal such as potassium triphosphate. Preferably, and to obtain even better results, the alkaline agent is sodium hydride.

In an embodiment, the suitable solvents for the preparation of the compound of formula VII according to the invention are selected from polar aprotic cyclic urea solvents such as DMI and 1,3-dimethyl-3,4,5,6-tetrahydro-2-pyrimidinone (DMPU). Preferably, and to obtain even better results, the solvent is DMI.

In an embodiment, preferably the molar ratio between the cyclization reaction components alkaline agent, intermediate VI, and compound X is between 1:1:1 and 5:1:3, more preferably, and to obtain even better results, it is 4:1:2 (see Table 1).

In an embodiment, the cyclization reaction occurs at a temperature between 50° C. and 120° C., preferably at 60° C.

In an embodiment, the cyclization reaction occurs for 1 to 20 hours, preferably 1 to 5 hours, more preferably 2 hours.

In an embodiment, the intermediate VII (S)-8-methyl-3-((S)-1-phenylethyl)-2,3,3a,4,5,6-hexahydro-1H-pyrazino[3,2,1-jk]carbazole obtained by a process according to the invention can be subjected to catalytic hydrogenolysis or acidic phenyl ethyl cleavage. Catalytic hydrogenolysis in acidified organic solvent mixture affords compound of formula III (S)-Pirlindole. Catalytic hydrogenolysis is under hydrogen pressure or under transfer hydrogenolysis conditions.

In an embodiment, the intermediate IX (R)-8-methyl-3-((R)-1-phenylethyl)-2,3,3a,4,5,6-hexahydro-1H-pyrazino[3,2,1-jk]carbazole obtained by a process according to the invention can be subjected to catalytic hydrogenolysis or acidic phenyl ethyl cleavage. Catalytic hydrogenolysis in acidified organic solvent mixture affords compound of formula II (R)-Pirlindole. Catalytic hydrogenolysis is under hydrogen pressure or under transfer hydrogenolysis conditions.

In an embodiment, preferably the acidic phenyl ethyl cleavage is conducted by an acidic cleavage agent such as boron or aluminium trihalide. More preferably the acidic cleavage agent is boron trichloride, boron tribromide or aluminium chloride.

In an embodiment, preferably the catalytic hydrogenolysis uses heterogeneous catalyst and occurs under hydrogen pressure. Preferably the heterogeneous catalyst is palladium on charcoal. More preferably the heterogeneous catalyst will have a palladium content of approximately 3.2 mol %. Preferably the hydrogen pressure for catalytic hydrogenolysis is between 500-2000 KPa (5-20 bar), more preferably it is 700 KPa (7 bar). Preferably the temperature for catalytic hydrogenolysis can be between 20-70° C. More preferably the temperature is 50° C. Preferably the catalytic hydrogenolysis lasts for a period of 2 to 8 hours, more preferably 5 hours. Suitable catalytic hydrogenolysis acidified solvent mixture can be a mixture of organic solvents selected from ethylacetate, DMF, MeOH, ethanol, isopropanol (iPrOH) and DCM, preferably the solvent mixture is composed of a mixture of a protic solvent with DCM, more preferably MeOH with DCM.

In an embodiment, the catalytic hydrogenolysis is carried out at 20-70° C., preferably for 2-8 hours and with an hydrogen pressure between 500-2000 KPa (5-20 bar).

In an embodiment, acidification of the solvent mixture preferably occurs by absorption of HCl gas.

In an embodiment, the high purity crude compound of formula III, or formula II, obtained does not require any base neutralization and is promptly recrystallized from water and/or a protic solvent.

One specific embodiment of the present invention is a process including the following steps:
  placing compound of formula X in DMI;
  carefully adding alkali metal hydride;
  adding a mixture of (S)-6-methyl-N—((S)-1-phenylethyl)-2,3,4,9-tetrahydro-1H-carbazol-1-amine (compound of formula VI) or (R)-6-methyl-N—((R)-1-phenylethyl)-2,3,4,9-tetrahydro-1H-carbazol-1-amine (compound of formula VIII) in DMI into the combination obtained before at a temperature and for a time sufficient to allow reaction to occur;
  adding MeOH to ice-water cooled reaction mixture in the previous step;
  allowing the suspension to stir at 0° C.;
  filtering the solid compound of formula VII or compound of formula IX and washing with water-MeOH;
  extracting the mother liquor with DCM;
  evaporating the DCM to leave recovered DMI solvent;
  subjecting the compound of formula VII or compound of formula IX to catalytic hydrogenolysis to obtain the salt form of compound of formula III or of compound of formula II.

The process of the invention is suitable for industrial use and presents an ecological advantage such as the possibility of recycling the solvent involved in the process (DMI).

The pharmaceutically accepted salts according to the invention include therapeutically active, non-toxic acid salt form which the compounds of formula II and III are able to form.

In an embodiment, the acid addition salt form of a compound of formula II or III that occurs in its free form as a base can be obtained by treating the free base with an appropriate acid such as an inorganic acid, for example hydrochloric, hydrobromic, sulphuric, phosphoric, nitric acid and the like; or an organic acid, such as, for example, acetic, citric, citric anhydrous, mandelic, hydroxyacetic, lactic, pyruvic, maleic, malonic, fumaric, malic, methanesulfonic, succinic, tartaric, glutamic, p-toluenesulfonic, cyclamic, ethanesulfonic, 1,2-ethanedisulfonic acid and the like.

In an embodiment, salt form can be converted into the free form by treatment with base.

In an embodiment, compounds of formula II or III, and their salts can be in the form of a solvate, which is included within the scope of the present invention. Such solvates include for example hydrates, alcoholates and the like.

In all the above mentioned scopes the optically active centre can assume both the configuration 'R'- or 'S'-.

Compounds of formula I, II and III and all the intermediates have one or two stereogenic centres in their structure. This stereogenic center may be present in an R or a S configuration, said R and S notation is used in correspondence with the rules described in Pure Appl. Chem. 45 (1976) 11-30.

The invention relates to all stereoisomeric forms such as enantiomeric and diastereomeric forms of the compounds of formula I, II and III and intermediates.

In an embodiment, the preparation of the compound of formula III or compound of formula II starting from compound of formula IV may be performed in a series of separate reactions whereby each intermediate is isolated, or may be performed as a telescopic synthesis.

For the purposes of this invention, it is considered as enantiomerically pure when enantiomeric purity is equal to or greater than 97%.

In an embodiment, the preparation of (S)-8-methyl-3-((S)-1-phenylethyl)-2,3,3a,4,5,6-hexahydro-1H-pyrazino[3,2,1-jk]carbazole, compound of formula VII was carried out as follow.

In an embodiment, in a 2 L three necked round bottomed flask equipped with magnetic stirrer, ethylene glycol ditosylate (73 g, 197 mmol) and DMI (240 mL) were loaded. To the resulting clear solution, NaH (60% suspension in mineral oil, 15.8 g, 394 mmol) was added carefully. To the resulting suspension a solution of VI ((S)-6-methyl-N-((S)-1-phenylethyl)-2,3,4,9-tetrahydro-1H-carbazol-1-amine) (30 g, 98.5 mmol) in DMI (60 mL) was added dropwise at 60° C. The mixture was stirred for 1 h at 60° C. The mixture was cooled down to room temperature, then MeOH was added slowly with ice-water cooling. A white precipitation appeared, and the resulting suspension was stirred and then filtered. The filtered product was washed with water-MeOH. The product was dried under vacuum to give 24.9 g of compound of formula VII (75.2 mmol, yield: 76%). Purity >99.9 area % (H PLC).

In an embodiment, the preparation of hydrochloride salt of (S)-Pirlindole, compound of formula III, was performed as follow.

In an embodiment, the free amine VII ((S)-8-methyl-3-((S)-1-phenylethyl)-2,3,3a,4,5,6-hexahydro-1H-pyrazino[3,2,1-jk]carbazole) (8.32 g, 25 mmol) was dissolved in DCM (42 mL) and excess of HCl in MeOH (42 mL) was added. The solvents were evaporated under reduced pressure to dryness to give a yellow oil. The residue was dissolved in MeOH (120 mL) and was added to the dispersion of Pd/C (1.74 g, ~50% water) in MeOH (20 mL). The reaction mixture was stirred at 50° C. under a 750 KPa (7.5 bar) pressure of hydrogen for 5 h. After completion (HPLC) the suspension was filtered through a celite pad, and the filter cake was washed with MeOH. The pH of the resulting solution was checked (<3) and it was evaporated to give the crude hydrochloride salt of compound of formula III. To the crude material iPrOH was added and the suspension was allowed to stir at reflux. The suspensions were filtered, and the product was dried under vacuum to give the hydrochloride salt of (S)-Pirlindole, compound of formula III (5.11 g, 19.5 mmol, yield: 77%). Purity >99.5% (HPLC). Enantiomeric purity 99.5% (Chiral HPLC). MS (ESI): m/z 227.2 $(M+)^+$.

The data disclosed in Tables 1 and 2 comprises isolated yields or reaction conversions. Reaction conversion reflects the conversion of the reactant into the product, can be obtained by HPLC analysis and indicated as area %.

In an embodiment, the combination of DMI, and in particular the use of DMI and the molar ratio of 1:1:1 of the alkaline agent: intermediate VI or VIII: compound of formula X, provides an unexpected increase in the yield and in the reaction conversion of compound VI or VIII into compound VII or IX, respectively. Preferably, for even better results use of DMI and the molar ratio of 1.2:1:1-4:1:2 of the alkaline agent: intermediate VI or VIII: compound of formula X, provides an unexpected increase in the yield and in the reaction conversion of compound VI or VIII into compound VII or IX, respectively.

In an embodiment and to obtain even better results, the combination of DMI and the molar ratios disclosed in Tables 1 and 2 surprisingly provide even higher yields and comparative reaction conversions of compound VI or VIII into compound VII or IX, respectively.

TABLE 1

Comparative yields using DMI as a solvent

| Molar ratio alkaline agent:intermediate VI or VIII:compound of formula X | Yield (%) of compound VI or VIII into compound VII or IX, respectively | Reaction conversion (%) of compound VI or VIII into compound VII or IX, respectively |
|---|---|---|
| 1.2:1:1 | 31 | 54[a] |
| 2.2:1:1.2 | — | 60[a] |
| 3:1:1.2 | — | 67[a] |
| 4:1:1.2 | — | 70[a] |
| 4:1:1.5 | — | 75[a] |
| 4:1:2 | 76 | 99.6[a] |

[a]Conversion of the reactant was determined by HPLC analysis [area %].

TABLE 2

Comparative yields using a molar ratio alkaline agent:intermediate VI or VIII:compound of formula X of 1.2:1:1 with different solvents

| Solvent | Yield (%) of compound VI or VIII into compound VII or IX, respectively |
|---|---|
| DMSO | 23.8 |
| DMI | 31 |

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

The invention claimed is:

1. A process for the synthesis of a pharmaceutically acceptable salt of (R)-Pirlindole of formula II:

<chemical structure of formula II: H3C-substituted tetracyclic indole with NH> wherein the process comprises the following steps:
1) cyclizing a compound of formula VIII:

<chemical structure of formula VIII> with a compound of formula X:

<chemical structure of formula X: L-CH2CH2-L> wherein:
L is Cl, Br, I, OS(O)$_2$CH$_3$, OS(O)$_2$CF$_3$, or OS(O)$_2$-Ph-(CH$_3$);
in the presence of 1,3-dimethyl-2-imidazolidinone and an alkaline agent selected from the group consisting of an alkali metal carbonate and an alkali metal hydride, to provide a compound of formula IX:

<chemical structure of formula IX> and 2) reacting the compound of formula IX above under catalytic hydrogenolysis comprising hydrogen in the presence of Pd/C and an excess of an acid selected from the group consisting of acetic acid, citric acid, ethanesulfonic acid, glutamic acid, hydrobromic acid, hydrochloric acid, lactic acid, maleic acid, malonic acid, mandelic acid, methanesulfonic acid, phosphoric acid, succinic acid, and tartaric acid, to provide the pharmaceutically acceptable salt of (R)-Pirlindole of formula II above.

2. The process according to claim 1, wherein the molar ratio of the alkaline agent to the compound of formula VIII to the compound of formula X is in the range of 1:1:1 to 5:1:3.

3. The process according to claim 2, wherein the molar ratio of the alkaline agent to the compound of formula VIII to the compound of formula X is in the range of 1.2:1:1 to 5:1:3.

4. The process according to claim 3, wherein the molar ratio of the alkaline agent to the compound of formula VIII to the compound of formula X is in the range of 2.2:1:1.2 to 4:1:2.

5. The process according to claim 4, wherein the molar ratio of the alkaline agent to the compound of formula VIII to the compound of formula X is in the range of 3:1:1.2 to 4:1:1.5.

6. The process according to claim 5, wherein the molar ratio of the alkaline agent to the compound of formula VIII to the compound of formula X is in the range of 3:1:1.2 to 4:1:1.2.

7. The process according to claim 1, wherein the molar ratio of the alkaline agent to the compound of formula VI to the compound of formula X is 4:1:2.

8. The process according to claim 1, wherein the alkaline agent is sodium hydride.

9. The process according to claim 1, wherein L is OS(O)$_2$-Ph-(CH$_3$).

10. The process according to claim 1, wherein the compound of formula X is:

<chemical structure: ditosylate of ethylene glycol>

11. The process according to claim 1, wherein the pharmaceutically acceptable salt of (R)-Pirlindole of formula II is formed by reacting the compound of formula IX under catalytic hydrogenolysis comprising hydrogen in the presence of Pd/C and an excess of hydrochloric acid.

12. The process according to claim 1, wherein the cyclization is performed at a temperature in the range of 50° C. to 120° C.

13. The process according to claim 1, wherein the catalytic hydrogenolysis is performed at a temperature in the range of 20° C. to 70° C. under a hydrogen pressure in the range of 500 kPa to 2000 kPa over a period of two to eight hours.

14. The process according to claim 1, wherein the pharmaceutically acceptable salt of (R)-Pirlindole of formula II is selected from the group consisting of the acetate salt, the citrate salt, the ethanesulfonate salt, the hydrobromide salt, the hydrochloride salt, the lactate salt, the maleate salt, the malonate salt, the mandelate salt, the methanesulfonate salt, the phosphate salt, the succinate salt, and the tartrate salt.

15. A process for the synthesis of a pharmaceutically acceptable salt of (S)-Pirlindole of formula III:

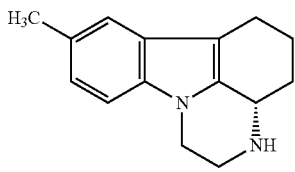

wherein the process comprises the following steps:
1) cyclizing a compound of formula VI:

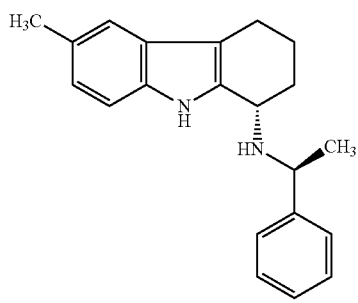

with a compound of formula X:

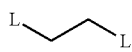

wherein:
L is Cl, Br, I, OS(O)$_2$CH$_3$, OS(O)$_2$CF$_3$, or OS(O)$_2$-Ph-(CH$_3$);
in the presence of 1,3-dimethyl-2-imidazolidinone and an alkaline agent selected from the group consisting of an alkali metal carbonate and an alkali metal hydride, to provide a compound of formula VII:

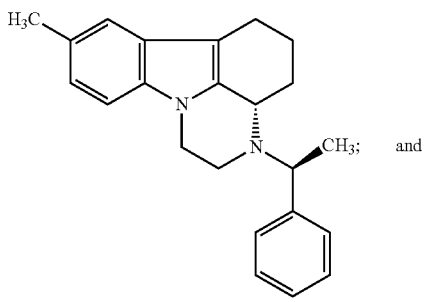

2) reacting the compound of formula VII above under catalytic hydrogenolysis comprising hydrogen in the presence of Pd/C and an excess of an acid selected from the group consisting of acetic acid, citric acid, ethanesulfonic acid, glutamic acid, hydrobromic acid, hydrochloric acid, lactic acid, maleic acid, malonic acid, mandelic acid, methanesulfonic acid, phosphoric acid, succinic acid, and tartaric acid, to provide the pharmaceutically acceptable salt of (S)-Pirlindole of formula III above.

16. The process according to claim 15, wherein the molar ratio of the alkaline agent to the compound of formula VI to the compound of formula X is in the range of 1:1:1 to 5:1:3.

17. The process according to claim 16, wherein the molar ratio of the alkaline agent to the compound of formula VI to the compound of formula X is in the range of 1.2:1:1 to 5:1:3.

18. The process according to claim 17, wherein the molar ratio of the alkaline agent to the compound of formula VI to the compound of formula X is in the range of 2.2:1:1.2 to 4:1:2.

19. The process according to claim 18, wherein the molar ratio of the alkaline agent to the compound of formula VI to the compound of formula X is in the range of 3:1:1.2 to 4:1:1.5.

20. The process according to claim 19, wherein the molar ratio of the alkaline agent to the compound of formula VI to the compound of formula X is in the range of 3:1:1.2 to 4:1:1.2.

21. The process according to claim 15, wherein the molar ratio of the alkaline agent to the compound of formula VI to the compound of formula X is 4:1:2.

22. The process according to claim 15, wherein the alkaline agent is sodium hydride.

23. The process according to claim 15, wherein L is OS(O)$_2$-Ph-(CH$_3$).

24. The process according to claim 15, wherein the compound of formula X is:

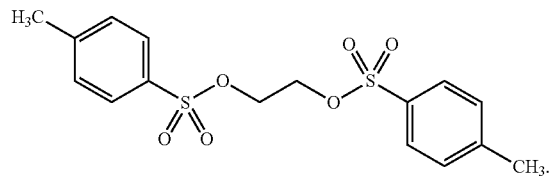 [SMILES: Cc1ccc(S(=O)(=O)OCCOS(=O)(=O)c2ccc(C)cc2)cc1]

25. The process according to claim 15, wherein the pharmaceutically acceptable salt of (S)-Pirlindole of formula III is formed by reacting the compound of formula VII under catalytic hydrogenolysis comprising hydrogen in the presence of Pd/C and an excess of hydrochloric acid.

26. The process according to claim 15, wherein the cyclization is performed at a temperature in the range of 50° C. to 120° C.

27. The process according to claim 15, wherein the catalytic hydrogenolysis is performed at a temperature in the range of 20° C. to 70° C. under a hydrogen pressure in the range of 500 kPa to 2000 kPa over a period of two to eight hours.

28. The process according to claim 15, wherein the pharmaceutically acceptable salt of (S)-Pirlindole of formula III is selected from the group consisting of the acetate salt, the citrate salt, the ethanesulfonate salt, the hydrobromide salt, the hydrochloride salt, the lactate salt, the maleate salt, the malonate salt, the mandelate salt, the methanesulfonate salt, the phosphate salt, the succinate salt, and the tartrate salt.

* * * * *